United States Patent
Pearson et al.

(10) Patent No.: US 7,341,347 B2
(45) Date of Patent: Mar. 11, 2008

(54) FUNDUS IMAGE DISPLAY SYSTEM

(75) Inventors: Ken Jo Pearson, Torrance, CA (US); Yutaka Mizukusa, Tokyo (JP)

(73) Assignees: Kowa Optimed, Inc.; Kowa Company, Ltd. (JP)

( * ) Notice: Subject to any disclaimer, the term of this patent is extended or adjusted under 35 U.S.C. 154(b) by 0 days.

(21) Appl. No.: 11/503,701

(22) Filed: Aug. 14, 2006

(65) Prior Publication Data

US 2007/0188706 A1    Aug. 16, 2007

(51) Int. Cl.
*A61B 3/14* (2006.01)
(52) U.S. Cl. ............................ 351/206; 351/210
(58) Field of Classification Search ............ 351/200, 351/205, 206, 210, 246
See application file for complete search history.

(56) References Cited

U.S. PATENT DOCUMENTS 6,224,212 B1 *  5/2001  Noda et al. ............ 351/206
6,598,970 B2 *  7/2003  Itoh ....................... 351/206

FOREIGN PATENT DOCUMENTS

| JP | 2004-081255 | 3/2004 |
| JP | 2004-272906 | 9/2004 |
| JP | 2006-26215  | 2/2006 |

* cited by examiner

*Primary Examiner*—Huy Mai
(74) *Attorney, Agent, or Firm*—Brian L. Belles; Wolf, Block, Schorr and Solis-Cohen LLP

(57) ABSTRACT

In a fundus image display system, a fundus image, time information and a tool bar are displayed on a monitor screen. In case where the tool bar overlaps with the fundus image or the time information, the tool bar is made transparent in the overlapped portion so at to perceive the fundus image and the time information with eyes, and a smooth diagnosis is possible, watching the fundus image, thereby.

2 Claims, 4 Drawing Sheets

FUNDUS IMAGE DISPLAY SYSTEM

BACKGROUND OF THE INVENTION

The invention relates to a fundus image display system for displaying a fundus image.

A fundus image display system for displaying a fundus image photographed with a fundus camera on a monitor screen of a personal computer have been widely used in order to find or diagnose macular degeneration or retinal blood infarction (see Japanese patent application publication number of which is 2006-26215).

A fluorescein fundus angiography (FAG) wherein a blood stream of a retina is photographed with a fluorescence dye is known as a photography of such a fundus image (see Japanese patent application publication number of which is 2004-81255). In such a fluorescein fundus angiography, a fluorescence dye, such as fluorescein, is injected into a vein of an examinee in such a state an eye to be examined can be photographed by a fundus camera. In such a case, the dye goes round in the body along the blood stream, and then, streams into a blood vessel of the retina. By registering the fundus images, corresponding to a passage time from the injection, it is possible to correctly confirm a presence of diseases and a proceeding state thereof. For this reason, time information, such as a passage time after giving the fluorescent dye, is displayed on the monitor screen together with the fundus image.

FIG. 4 is a typical view showing a conventional state where a monitor screen of a personal computer displays a fundus image wherein a reference numeral 103 denotes the monitor screen of the personal computer, a reference numeral 131 denotes the fundus image, a reference numeral 132 denotes time information and a reference numeral 133 denotes a tool bar.

With such a monitor screen, there is such a problem that an overlap between the fundus image 131 or the tool information 132 and the tool bar 133 brings an obstruction in a diagnosis.

Then, an insertion of the tool bar into a frame is thinkable. But, it is necessary to broaden the display area of the frame in order to do so, and the display area itself of the photographed fundus image may be made smaller thereby.

The object of the invention is to provide a fundus image display system having no overlap between the fundus image or the time information and the tool bar.

SUMMARY OF THE INVENTION

On aspect of the invention is fundus image display system for displaying a fundus image on a monitor screen, comprising:
- a fundus image display unit for displaying a fundus image as a color image and/or a fluorescent image on said monitor screen;
- a time information display unit for displaying time information on said monitor screen in case where said fundus image to be displayed is said fluorescent image;
- a tool bar display unit for displaying a tool bar on said monitor screen;
- a fundus image display area detector for detecting a display area of said fundus image on said monitor screen;
- a time information display area detector for detecting a display area of said time information on said monitor screen;
- a tool bar display area detector for detecting a display area of said tool bar on said monitor screen;
- a display area judging unit for judging whether or not said display area of said tool bar overlaps with said display area of said fundus image or said time information; and
- a tool bar transparency adjuster for raising a transparency of at least overlapped portion between said display area of said tool bar and said display area of said fundus image or said time information so as to perceive said fundus image and said time information with eyes if said display area judging unit judges said overlap.

According to this aspect of the invention, the fundus image and the time information can be perceived with eyes even in the portion overlapped with the tool bar, and a smooth diagnosis is possible, thereby.

The other aspect of the invention is the fundus image display system, wherein said fundus image display system further has a cursor display position detector for detecting a position on said monitor screen where a cursor is displayed, and said tool bar transparency adjuster lowers said transparency of a portion said transparency of which has been raised so as to be perceived with eyes if said cursor approaches said portion.

According to this aspect of the invention, the tool bar clearly emerges from obscurity when the cursor approaches, and there is no obstruction when clicking a function button of the tool bar, maintaining the above-mentioned effects, that is, smooth diagnosis by confirming the fundus image or the time information with eyes.

DESCRIPTION OF THE PREFERRED EMBODIMENTS

Embodiments of the invention will now be explained, referring to appended figures.

A fundus image display system according to the invention is a system for displaying a fundus image on a monitor screen of a personal computer.

Figure 1:
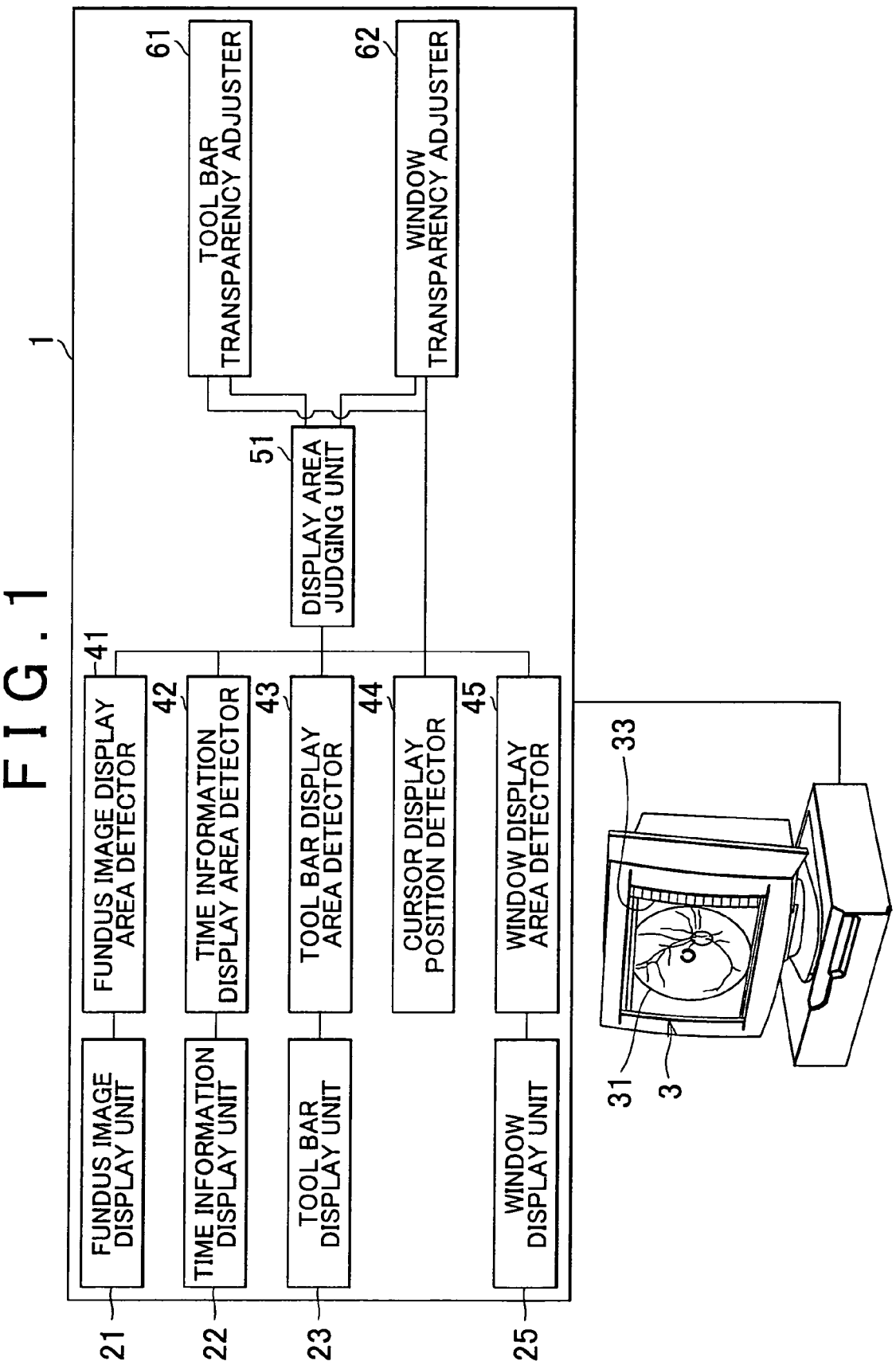
FIG. 1 is a block diagram showing an instance of the whole structure of a fundus image display system according to the invention.

The fundus image display system is exemplarily shown with a reference numeral 1 of FIG. 1, and displays a fundus image 31 by a fundus image display unit 21 as a color image and/or a fluorescent image on a monitor screen 3.

And, this fundus image display system 1 has a time information display unit 22 for displaying time information (see a reference numeral 32 of FIG. 2) on the monitor screen 3 in order to display time information, such as elapsed time after giving fluorescence dye if the displayed fundus image is a fluorescent image. Besides, the fundus image display system 1 also displays a tool bar 33 on the monitor screen 3 by a tool bar display unit 23.

The fundus image display system 1 according to the invention has a fundus image display area detector 41, a time information display area detector 42 and a tool bar display area detector 43 for respectively detecting display areas of the fundus image 31 and the time information 32 and the tool bar 33 on the monitor screen. These detectors 41, 42 and 43 are ones having broad conception, and include a unit for manually inputting each display area by an operator, in addition to a unit for monitoring some physical amount all the time, such as a common sensor.

Besides, the fundus image display system 1 according to the invention has a display area judging unit 51 for judging whether or not the display area of the tool bar 33 overlaps with the display area of the fundus image 31 or the time information 32. If the display area judging unit 51 judges both overlap between the display areas of the tool bar 33 and the fundus image 31 and the overlap between the display areas of the tool bar 33 and the time information 32 or one of both, a tool bar transparency adjuster 61 raises a transparency so as to perceive the fundus image 31 or the time information 32 with eyes in the overlapped portion. In the invention, it is sufficient to partially raise the transparency of only overlapped portion. But, such a case where the transparency of a non-overlapping portion is also raised together with the overlapped portion is not excluded from the invention. In such a case, it is possible to perceive the fundus image or the time information with eyes also in the portion overlapped with the tool bar 33, and a diagnosis can be smoothly executed thereby.

And, the system 1 according to the invention may have a cursor display position detector 44 for detecting a position where a cursor (see a reference numeral 34 of FIG. 2) moving on the monitor screen with a well-known mouse or a touch pen is displayed in order to lower the transparency of the portion which was raised in its transparency so as to perceive with eyes if the cursor 34 approaches the portion. With such a structure, the tool bar clearly emerges from obscurity when the cursor 34 approaches, and there is no obstruction when clicking a function button of the tool bar, maintaining the above-mentioned effects, that is, smooth diagnosis by confirming the fundus image or the time information with eyes.

Figure 3:
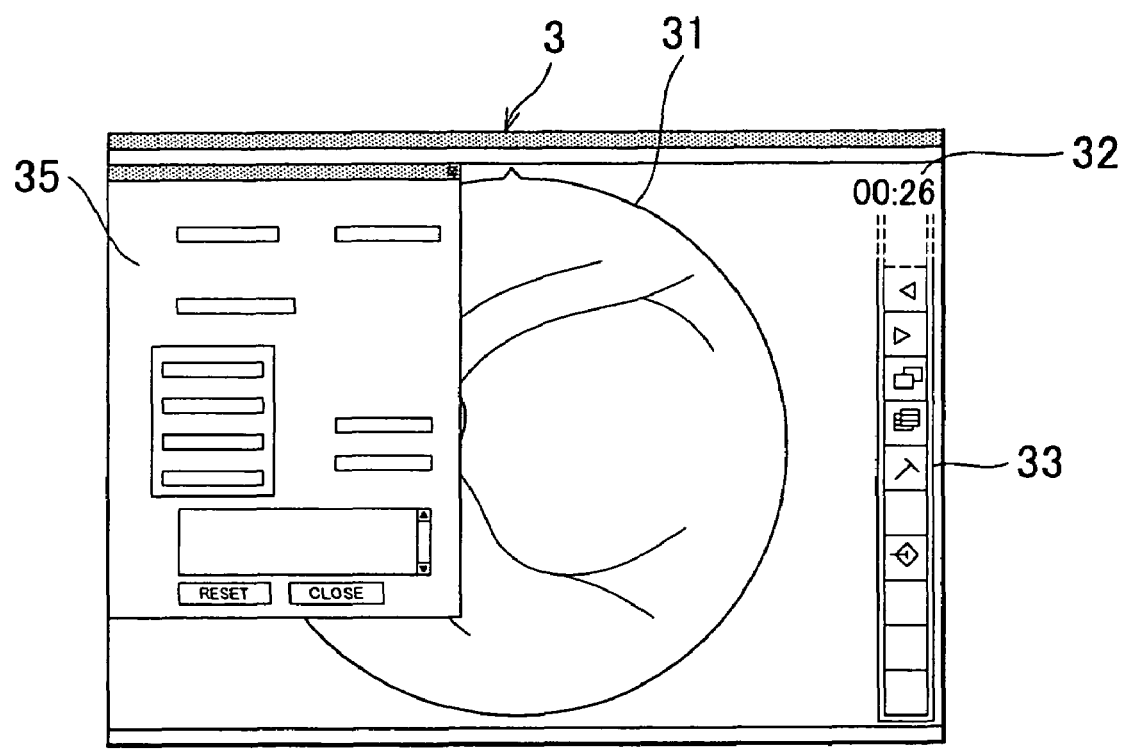
FIG. 3 is a schematic view showing the other instance of the monitor screen displayed.

Besides, the system 1 according to the invention may have a window display unit 25 for displaying a window, such as a data base list (see a reference numeral 35 of FIG. 3) on the monitor screen, a window display area detector 45 for detecting the display area of the displayed window 35, and a window transparency adjuster 62 for adjusting the transparency of the window 35 so that the display area judging unit 51 can judge whether or not the display area of the window 35 overlaps with the display area of the fundus image 31 or the display area of the time information 32, and the window transparency adjuster 62 can raise the transparency of the overlapped portion if overlaps.

Besides, also in the window 35, the transparency of the window 35 may be lowered in a similar way to the above-mentioned if the cursor 34 approaches.

Preferably, the transparency adjustable by the respective transparency adjusters 61, 62 can be properly changed. For instance, the transparency may be changed through an operation of a scroll button of a mouse.

When displaying information on photographic conditions on the monitor screen, the transparency of the tool bar 33 or the window 35 is raised in the display area of the information, preferably.

Figure 4:
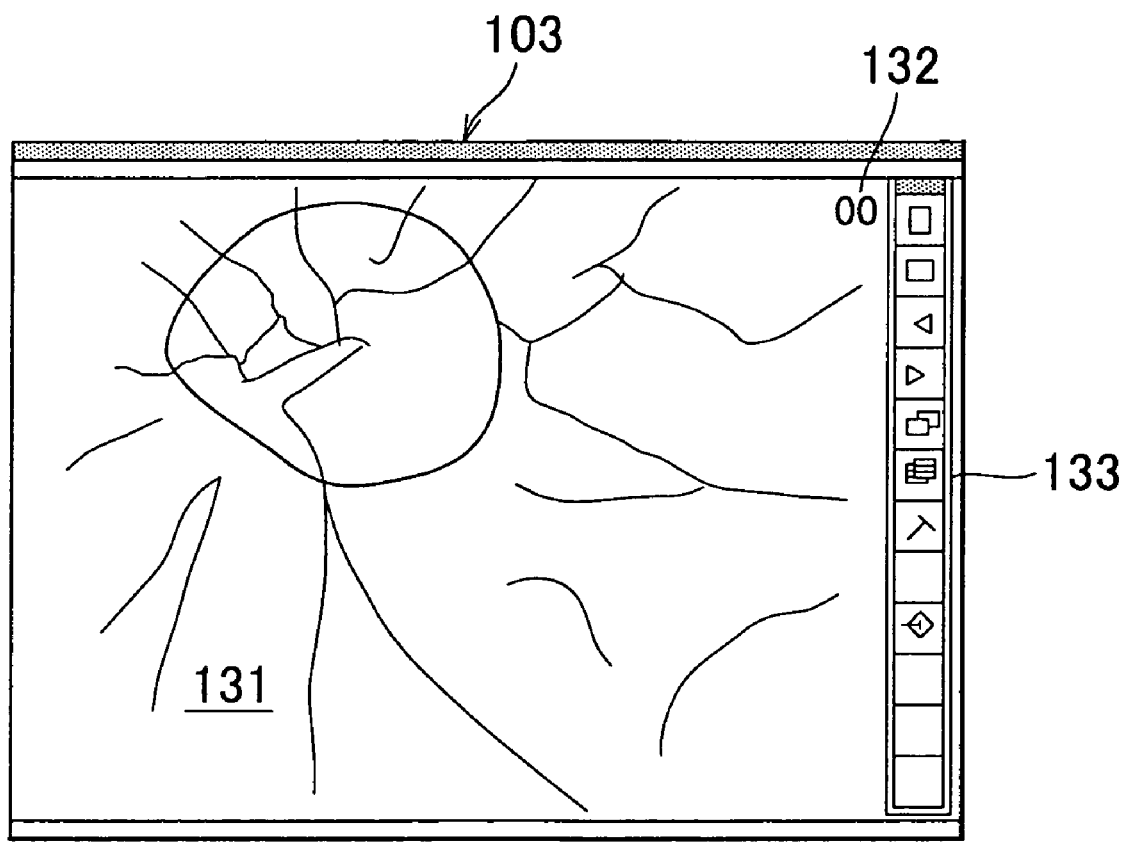
FIG. 4 is a schematic view showing a conventional state where the monitor screen of a personal computer displays the fundus image.

The above-mentioned fundus image display unit 21 may display the fundus image photographed at wide angle (see the reference numeral 31 of FIG. 2) on the monitor screen (a central portion of the screen excluding an upper edge, a lower edge, a left edge and a right edge), the fundus image photographed at high magnification on the almost whole screen (see the reference numeral 131 of FIG. 4) or the fundus image with multiple screens (not shown).

First Embodiment

In this embodiment, the fundus image display system 1 having the structure as shown in FIG. 1 is used. Then, the fundus image display unit 21 can display (1) a fluorescent image photographed at wide angle, (2) a fluorescent image photographed at high magnification (mydriatic image), (3) a color image photographed at wide angle, (4) a color image photographed at high magnification (non-mydriatic image) and (5) a color image photographed at high magnification (mydriatic image) through an instruction of an operator.

As mentioned above, the display area of each fundus image 31 is detected by the fundus image display area detector 41. In case of the image photographed at wide angle, such as (1) and (3), the fundus image display area is the area of the monitor screen 3 excluding areas adjacent to the respective edges of the monitor screen 3 (that is, the areas along the upper edge, the lower edge, the left edge and the right edge on the monitor screen), in other words, the central portion of the screen. In case of the image photographed at high magnification, such as (2), (4), (5), the almost whole screen is the fundus image display area.

Figure 2:
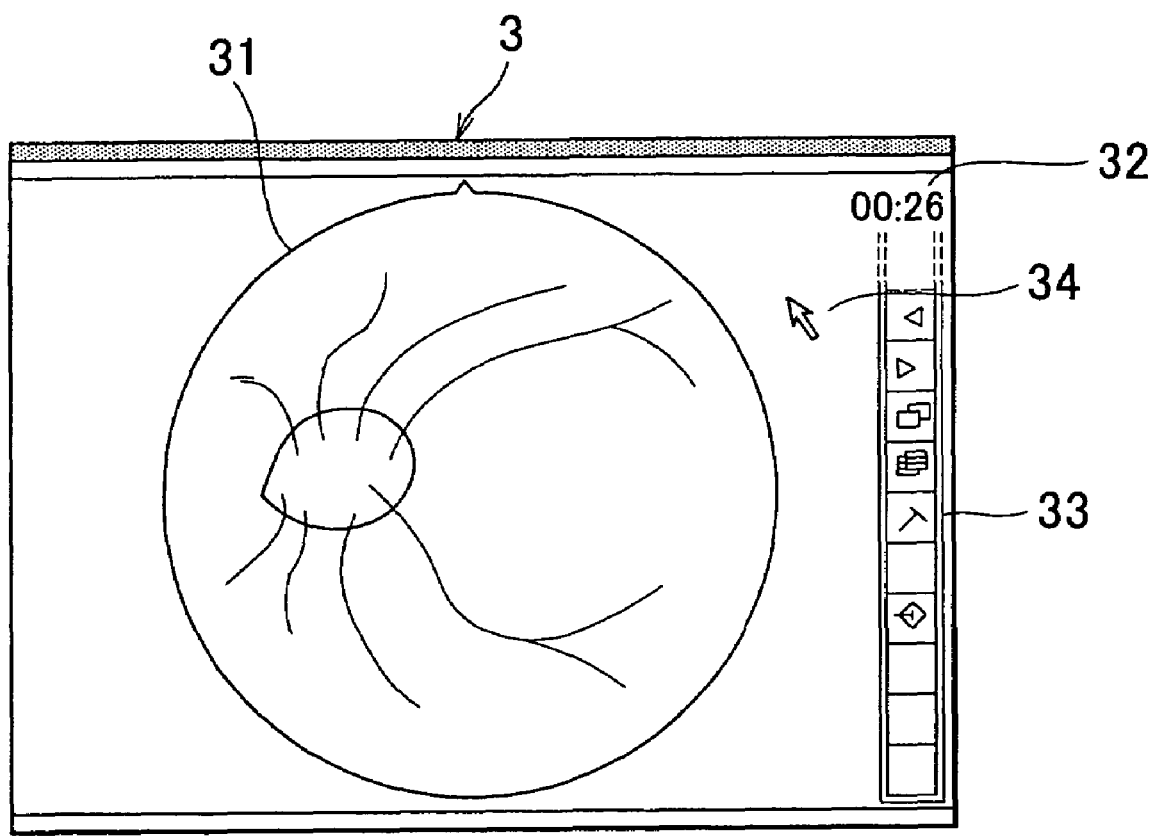
FIG. 2 is a schematic view showing an instance of a monitor screen displayed.

And, the time information display unit 22 displays the time information on the right upper portion of the monitor screen when the fluorescent image (1) or (2) being displayed (see the reference numeral 32 of FIG. 2). The display area of the time information is detected by the time information display area detector 42 as mentioned before, and the right upper edge is always the display area.

In this embodiment, the tool bar display unit 23 displays the tool bar 33 along the right edge of the monitor screen 3 when any image (1) through (5) being displayed, as shown in FIG. 2. In other words, the tool bar display area to be detected by the tool bar display area detector 43 is the area along the right edge of the monitor screen.

In case of the above-mentioned (1), the tool bar display area overlaps with only the time information display area, so that only the overlapped portion is made transparent by the tool bar transparency adjuster 61, and the tool bar in the other portion is maintained so as to be perceived with eyes (see (1) of a chart shown below).

In a case where the fundus image is not the fluorescent image, but the color image, the time information is not displayed, so that there is no overlap between the tool bar display area and the fundus image display area and between the tool bar display area and the time information display area. Therefore, it is completely unnecessary to adjust the transparency by the tool bar transparency adjuster 61, and the whole tool bar is displayed so as to be perceived with eyes (see the above-mentioned (3)).

In case of the above-mentioned (4) photographed at high magnification, the mydriatic fundus image is displayed on the whole monitor screen, so that it is necessary to make the whole tool bar transparent (see (4) of the chart shown below).

In case of the above-mentioned (2), (5) photographed at high magnification, the mydriatic fundus image is displayed on the monitor screen, so that the whole tool bar is made transparent (see (2), (5) of the chart shown below).

| | How to display fundus image | |
|---|---|---|
| | Fluorescent Image | Color Image |
| Wide angled photography | (1) only time information display area is transparent | (3) the whole is displayed |
| High magnification photography (non-mydriatic) | — | (4) the whole is transparent |
| High magnification photography (mydriatic) | (2) the whole is transparent | (5) the whole is transparent |

The present invention is explained on the basis of the embodiment heretofore. The embodiments which are described in the present specification are illustrative and not limiting. The scope of the invention is designated by the accompanying claims and is not restricted by the descriptions of the specific embodiments. Accordingly, all the transformations and changes belonging to the claims are included in the scope of the present invention.

The invention claimed is:

1. Fundus image display system for displaying a fundus image on a monitor screen, comprising:

a fundus image display unit for displaying a fundus image as a color image and/or a fluorescent image on said monitor screen;

a time information display unit for displaying time information on said monitor screen in case where said fundus image to be displayed is said fluorescent image;

a tool bar display unit for displaying a tool bar on said monitor screen;

a fundus image display area detector for detecting a display area of said fundus image on said monitor screen;

a time information display area detector for detecting a display area of said time information on said monitor screen;

a tool bar display area detector for detecting a display area of said tool bar on said monitor screen;

a display area judging unit for judging whether or not said display area of said tool bar overlaps with said display area of said fundus image or said time information; and a tool bar transparency adjuster for raising a transparency of at least overlapped portion between said display area of said tool bar and said display area of said fundus image or said time information so as to perceive said fundus image and said time information with eyes if said display area judging unit judges said overlap.

2. The fundus image display system according to claim 1, wherein said fundus image display system further has a cursor display position detector for detecting a position on said monitor screen where a cursor is displayed, and said tool bar transparency adjuster lowers said transparency of a portion said transparency of which has been raised so as to be perceived with eyes if said cursor approaches said portion.

* * * * *